(12) United States Patent
Choi et al.

(10) Patent No.: US 12,251,375 B2
(45) Date of Patent: *Mar. 18, 2025

(54) PHARMACEUTICAL PREPARATION HAVING EXCELLENT DISSOLUTION PROPERTIES, CONTAINING ESOMEPRAZOLE AND SODIUM BICARBONATE

(71) Applicant: CHONG KUN DANG PHARMACEUTICAL CORP., Seoul (KR)

(72) Inventors: Jong Seo Choi, Yongin-Si Gyeonggi-Do (KR); Min Soo Kim, Yongin-Si Gyeonggi-Do (KR); Shin Jung Park, Yongin-Si Gyeonggi-Do (KR); Jong Lae Lim, Yongin-Si Gyeonggi-Do (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 755 days.

This patent is subject to a terminal disclaimer.

(21) Appl. No.: 17/270,263

(22) PCT Filed: Jul. 26, 2019

(86) PCT No.: PCT/KR2019/009371
§ 371 (c)(1),
(2) Date: Feb. 22, 2021

(87) PCT Pub. No.: WO2020/040438
PCT Pub. Date: Feb. 27, 2020

(65) Prior Publication Data
US 2022/0233514 A1 Jul. 28, 2022

(30) Foreign Application Priority Data
Aug. 23, 2018 (KR) .......... 10-2018-0098744

(51) Int. Cl.
*A61K 31/4439* (2006.01)
*A61K 9/16* (2006.01)
(Continued)

(52) U.S. Cl.
CPC ............ *A61K 31/4439* (2013.01); *A61K 9/16* (2013.01); *A61K 9/1676* (2013.01);
(Continued)

(58) Field of Classification Search
CPC .... A61K 31/4439; A61K 9/16; A61K 9/1676; A61K 9/2095; A61K 9/2893; A61K 9/5026; A61K 9/5047; A61K 9/5073
See application file for complete search history.

(56) References Cited

U.S. PATENT DOCUMENTS 6,183,776 B1 * 2/2001 Depui ................ A61P 1/00
424/468
6,369,085 B1 4/2002 Cotton et al.
(Continued)

FOREIGN PATENT DOCUMENTS

CN 1183047 A 5/1998
CN 1551768 A 12/2004
(Continued)

OTHER PUBLICATIONS

Howden., "Immediate-Release Omeprazole/Sodium Bicarbonate," Gastroenterology & Hepatology, 2(5): 386 (2006).
(Continued)

*Primary Examiner* — Jianfeng Song
(74) *Attorney, Agent, or Firm* — Foley Hoag LLP; David P. Halstead; Benjamin A. Vaughan (57) ABSTRACT

The present invention relates to a pharmaceutical preparation comprising omeprazole, an enantiomer thereof or a pharmaceutically acceptable salt thereof, and sodium bicarbonate, and a method for preparing the same. Specifically,
(Continued)

the present invention relates to a pharmaceutical preparation in which sodium bicarbonate is first disintegrated so as to raise pH, and then omeprazole is dissolved such that the release properties of an active ingredient are improved, and thus the dissolution pattern and bioavailability of a drug can be enhanced.

7 Claims, 7 Drawing Sheets

(51) Int. Cl.
  *A61K 9/20* (2006.01)
  *A61K 9/28* (2006.01)
  *A61K 9/50* (2006.01)
(52) U.S. Cl.
  CPC .......... *A61K 9/2095* (2013.01); *A61K 9/2893* (2013.01); *A61K 9/5026* (2013.01); *A61K 9/5047* (2013.01); *A61K 9/5073* (2013.01)

(56) References Cited

U.S. PATENT DOCUMENTS

| | | | |
|---|---|---|---|
| 11,759,428 | B2 | 9/2023 | Choi et al. |
| 11,813,285 | B2 | 11/2023 | Choi et al. |
| 2002/0045646 | A1 | 4/2002 | Phillips |
| 2004/0048896 | A1* | 3/2004 | Phillips ................. A61K 47/02 |
| | | | 424/468 |
| 2005/0239845 | A1 | 10/2005 | Proehl et al. |
| 2005/0266071 | A1 | 12/2005 | Olmstead et al. |
| 2007/0053981 | A1 | 3/2007 | Blychert et al. |
| 2009/0092658 | A1 | 4/2009 | Hall et al. |
| 2010/0029654 | A1 | 2/2010 | Pasinetti |
| 2012/0121664 | A1 | 5/2012 | Pettersson et al. |
| 2012/0128764 | A1 | 5/2012 | Venkatesh et al. |
| 2014/0271853 | A1 | 9/2014 | Hall et al. |
| 2015/0044303 | A1 | 2/2015 | Olmstead et al. |
| 2021/0030687 | A1 | 2/2021 | Choi et al. |
| 2021/0030786 | A1 | 2/2021 | Choi et al. |
| 2022/0233514 | A1 | 7/2022 | Choi et al. |

FOREIGN PATENT DOCUMENTS

| | | |
|---|---|---|
| CN | 101002769 A | 7/2007 |
| CN | 101036633 A | 9/2007 |
| CN | 101259108 A | 9/2008 |
| CN | 102078616 A | 6/2011 |
| CN | 102114035 A | 7/2011 |
| CN | 102397277 A | 4/2012 |
| CN | 103599082 A | 2/2014 |
| CN | 103784414 A | 5/2014 |
| CN | 103845734 A | 6/2014 |
| CN | 103860584 A | 6/2014 |
| CN | 103006691 B | 10/2014 |
| CN | 104523746 A | 4/2015 |
| CN | 204428461 U | 7/2015 |
| CN | 107913255 * | 4/2018 |
| EP | 0496437 A2 | 7/1992 |
| EP | 3236952 A1 | 11/2017 |
| JP | H11501950 A | 2/1999 |
| JP | 2003-073270 A | 3/2003 |
| JP | 2006/505566 A | 2/2006 |
| JP | 2006-528198 A | 12/2006 |
| JP | 2007526319 A | 9/2007 |
| JP | 2008/500365 A | 1/2008 |
| JP | 2008-504372 A | 2/2008 |
| JP | 2008-512453 A | 4/2008 |
| JP | 2009534441 A | 9/2009 |
| JP | 2011-512416 A | 4/2011 |
| JP | 2011530569 A | 12/2011 |
| JP | 2016-509061 A | 3/2016 |
| JP | 7003279 B2 | 1/2022 |
| KR | 100115254 B | 12/1995 |
| KR | 10-1996-0003605 B1 | 3/1996 |
| KR | 960003605 B1 | 3/1996 |
| KR | 100274698 B1 | 12/2000 |
| KR | 10-2002-0089322 A | 11/2002 |
| KR | 100384960 B1 | 8/2003 |
| KR | 10-2004-0047771 A | 6/2004 |
| KR | 20040047771 A | 6/2004 |
| KR | 10-2004-0099265 A | 11/2004 |
| KR | 2005/0061647 A | 6/2005 |
| KR | 100679767 B1 | 2/2007 |
| KR | 10-2010-0066742 A | 6/2010 |
| KR | 10-2011-0079641 A | 7/2011 |
| KR | 10-2011-0123178 A | 11/2011 |
| KR | 101104349 B1 | 1/2012 |
| KR | 10-2013-0115593 A | 10/2013 |
| KR | 20130115593 A | 10/2013 |
| KR | 10-2015-0083255 A | 7/2015 |
| KR | 10-2016-0020625 A | 2/2016 |
| KR | 20160020625 A | 2/2016 |
| KR | 10-2016-0082169 A | 7/2016 |
| KR | 10-2016-0124368 A | 10/2016 |
| KR | 10-2017-0076494 A | 7/2017 |
| KR | 20170076494 A | 7/2017 |
| KR | 10-2017-0126915 A | 11/2017 |
| KR | 10-2017-0136771 A | 12/2017 |
| KR | 10-2018-0010987 A | 1/2018 |
| KR | 10-2018-0011624 A | 2/2018 |
| KR | 20180011624 A | 2/2018 |
| KR | 10-2018-0098744 A | 9/2018 |
| KR | 20180098744 A | 9/2018 |
| KR | 10-2019-0003312 A | 1/2019 |
| KR | 20190003312 A | 1/2019 |
| KR | 10-2019-0037182 A | 4/2019 |
| KR | 20190037182 A | 4/2019 |
| KR | 10-2006777 B1 | 10/2019 |
| KR | 10-2080023 B1 | 2/2020 |
| KR | 20200089322 A | 7/2020 |
| KR | 10-2146395 | 8/2020 |
| MX | 2016011522 A | 3/2018 |
| WO | WO-2001/051050 A1 | 7/2001 |
| WO | WO-2003/009846 A1 | 2/2003 |
| WO | WO-2005/092297 A2 | 10/2005 |
| WO | WO-2008110070 A1 | 9/2008 |
| WO | WO-2016/024822 A1 | 2/2016 |
| WO | WO-2017/122212 A1 | 7/2017 |
| WO | WO-2019/146937 A1 | 8/2019 |
| WO | WO-2019/147094 A1 | 8/2019 |
| WO | WO-2020/040438 A1 | 2/2020 |

OTHER PUBLICATIONS

International Search Report for PCT Application No. PCT/KR2019/009371 dated Oct. 25, 2019.
International Search Report for PCT Application No. PCT/KR2020/009250, dated Oct. 15, 2020.
Xingguo, "Microcarrier Drug Delivery System", Wuhan, Huazhong University of Science and Technology Press, 4 pages (2009) (English translation).
Xingguo, "Microcarrier Drug Delivery System", Wuhan, Huazhong University of Science and Technology Press, 4 pages (2009).
"A randomized, open-label, multiple-dose, and three-way crossover clinical trial to compare pharmacokinetics and safety of CKD-381 and D026 in healthy male subjects", Chong Kun Dang Pharm., excerpt from clinical trial report.
Eso Duo Tablet Product Insert with partial English translation.
Excerpt from "Pharmaceutical Dosage Forms" relating to Granulation Processes with partial English translation, published Feb. 15, 2013, modified Feb. 15, 2015 (with partial English translation).
Excerpt from Korean Pharmacopia relating to dissolution test method (with partial English translation).
Experimental Report of Comparative Dissolution Tests on Eso Duo Tablets (with partial English translation).
Experimental Report of Comparative Stability of Chong Kun Dang Pharmecuritcals Corp. omeprazole sulfone tablets with Genuonesciences omeprazole sulfone tablets, (with English translation), 16 pages.
Experimental Report of Comparative test of FTC dissolution based on the amount of sodium bicarbonate in esomeprazole granule (with partial English translation).

(56) References Cited

OTHER PUBLICATIONS

Experimental Report of Comparative test of FTC dissolution of esomeprazole/sodium bicarbonate formulations (with partial English translation).
Experimental Report of FTC Dissolution Test of Eso Duo Tab. (40/800 mg) (with partial English translation).
Ganaflux Product Insert with partial English translation.
Gardner et al., "Integrated Acidity and the Pathophysiology of Gastroesophageal Reflux Disease", The American Journal of Gastroenterology, vol. 96, No. 5, 2001, pp. 1363-1370.
Information Sheet on Esoduo Tabs 20/800 mg, permit date Apr. 30, 2018, with English machine translation.
Information Sheet on Ganaflux Tab 40/1100 mg, date of approval Jun. 19, 2015 (with partial English translation).
Kim et al. "The safety, pharmacodynamics, and pharmacokinetics of immediate-release formulation containing esomeprazole 20 mg/sodium biocarbonate 800 mg in healthy adult male", Drug Design, Development and Therapy 2019:13, pp. 3151-3159.
Lee et al., "Effect of Other Medications on the Stability of Omeprazole in Aqueous Solution for the Peptic Ulcer Disease", Journal of the Korean Society of Industrial Science and Technology, vol. 10, No. 11, pp. 3494-3499, 2009 (with English abstract).
Mishra et al. "Formulation, Development and Evaluation of an Immediate Release Buffer Tablet of Omeprazole", Pharma Science Monitor 7(2), Apr.-Jun. 2016, pp. 270-281.
Newspaper Article from MedicalObserver.com describing Eso Duo Tab, dated Jul. 23, 2018, updated Mar. 24, 2021 (with partial English translation).
Newspaper Article from MedicalTimes.com describing Chong Kun Dang combination of esomeprazole and sodium bicarbonate, dated Jan. 26, 2018, accessed Mar. 26, 2021 (with partial English translation).
Newspaper Article from Yakup.com describing Ganaflux Tab (40-1100 mg), accessed Mar. 26, 2021 (with partial English translation).
Tutuian et al., "The acidity index: a simple approach to the measurement of gas acidity", Aliment Pharmacol Ther 2004; 19: pp. 443-448.
Yacyshyn et al., "The Clinical Importance of Proton Pump Inhibitor Pharmacokinetics", Digestion 2002; 66: pp. 67-78.
General Guidelines for the Clinical Evaluation of New Drugs, Jun. 29, 1992, 25 pages.
"Study Comparing Esomeprazole Associated With Sodium Bicarbonate From Eurofarma and Esomprazole in treatment of Gastroesophageal Reflux Disease ESOBIC," ClinicalTrials Identifier: NCT01471925 (2015).
Approval package NDA21153S-008 (Astrazeneca, Jan. 9, 2004).
Marketing Materials for OPADRYL amb II, published by Colorcon, 2 pages.
Levina et al., "The Influence of Film Coatings on Performance of Hypromellose Matrices", published by Colorcon, dated Feb. 5, 2020, 3 pages.
Protocol for Testing and Analysis of Nexoduo tablet 20/80mg, dated Oct. 5, 2021 (with English translation), 3 pages.
Experimental Report of Comparative Stability of Chong Kun Dang Pharmaceuticals Corp. omeprazole sulfone tablets with Genuonesciences omeprazole sulfone tablets, (with English translation), 16 pages.
Rowe et al., "Handbook of Pharmaceutical Excipients" Sixth Edition, Pharmaceutical Press, published 2009.
Certificate of Analysis for Opadry AMB II High Performance Moisture Barrier Film Coating 88A5400358 Pink, dated Mar. 30, 2020, 6 pages.
Clinical Trial to Evaluate the Efficacy and Safety of EsoDuo Tab. 20/800mg, Clinical Trial No. NCT03928470, last updated Dec. 24, 2019.
Office Action for Mexican Application No. MX/a/2021/001905 dated Jul. 18, 2023, with English Translation.
Office Action for Vietnamese Application No. 1-2021-00895 dated Aug. 29, 2023, with English Translation.

* cited by examiner

* Vertical axis : the ratio of the dissolution rate at each point to the maximum dissolution rate

[Figure 7]

* b is the AUC (area under the curve) of the dissolution rate of Example 5, and a is the AUC of each of Examples 5 to 10.

PHARMACEUTICAL PREPARATION HAVING EXCELLENT DISSOLUTION PROPERTIES, CONTAINING ESOMEPRAZOLE AND SODIUM BICARBONATE

RELATED APPLICATIONS

This application is the U.S. National Phase of International Patent Application No. PCT/KR2019/009371, filed Jul. 26, 2019, which claims the benefit of priority to Korean Patent Application No. KR 10-2018-0098744, filed Aug. 23, 2018. International Patent Application No. PCT/KR2019/009371 is incorporated herein by reference in its entirety.

TECHNICAL FIELD

The present invention relates to a pharmaceutical preparation comprising omeprazole, an enantiomer thereof or a pharmaceutically acceptable salt thereof, and sodium bicarbonate, and a method for preparing the same. Specifically, the present invention relates to a pharmaceutical preparation in which sodium bicarbonate is first dissolved so as to raise pH, and then esomeprazole is dissolved such that the release properties of an active ingredient are improved, and thus the dissolution pattern and bioavailability of a drug can be enhanced.

BACKGROUND ART

Omeprazole has a chemical name of 5-methoxy-2-[(4-methoxy-3,5-dimethyl-2-pyridinyl)methyl]sulfinyl-1H-benzimidazole. Omeprazole exists in the two types of isomers, i.e., R-isomer and S-isomer. S-isomer is known for being remarkably excellent in terms of the therapeutic effect and side effects in comparison with R-isomer. The S-isomer is (S)-5-methoxy-2-[(4-methoxy-3,5-dimethyl-2-pyridinyl)-methyl]sulfinyl-1H-benzimidazole, which is commonly called esomeprazole.

Esomeprazole is a representative proton pump inhibitor (PPI) which is used for the treatment of dyspepsia, peptic ulcer disease, gastroesophageal reflux disease, Zollinger-Ellison syndrome, and the like.

It is well known in the art that omeprazole, especially, esomeprazole, is prone to degradation or transformation in acidic media. More particularly, esomeprazole is known to have a degradation half-life of less than 10 minutes in an aqueous solution having a pH of 3 or less. Therefore, the degradation of esomeprazole is promoted by an acidic compound, and also affected by moisture, heat, organic solvents, and light. Thus, there have been a lot of demands on a stable esomeprazole preparation. In order to solve the stability issue, Korean Patent No. 10-0384960 discloses a method of preparing a pellet comprising a magnesium salt of esomeprazole, followed by enteric coating the same, adding excipients, and formulating as a tablet. The preparation manufactured by the method described above is currently being marketed under the trade name of Nexium.

However, an enteric coated tablet such as Nexium is not suitable for the treatment of diseases requiring immediate therapeutic effect after administration, such as gastric acid-related diseases, because it was designed to be dissolved and absorbed in the intestine while not causing immediate absorption in the stomach.

Korean Patent No. 10-1104349 discloses an enteric coated tablet and capsule in which the problem of the stability and physical properties of omeprazole was improved by preparing a solid dispersion formulation with magnesium oxide and povidone.

Korean Patent Publication No. 10-1996-0003605 discloses a method for preparing a solid dispersion formulation comprising omeprazole as an active ingredient in which beta-cyclodextrin and sodium hydroxide are added as a stabilizing ingredient. However, the invention described in the above patent has a problem of using sodium hydroxide which is harmful to human body. The process of preparing the solid dispersion includes dissolving the active ingredient, omeprazole, in a solvent, and thus during this process, a special stabilizing agent such as sodium hydroxide is required to stabilize omeprazole.

In order to solve these problems, Korean Patent No. 10-0679767 discloses a method of using a buffering agent such as sodium bicarbonate for omeprazole. However, the invention described in the above patent only discloses a combination preparation comprising omeprazole and sodium bicarbonate as a buffering agent at the same time, and does not solve the problem of degradation of omeprazole when omeprazole is disintegrated and dissolved in the gastric juice from these combination preparations.

DETAILED DESCRIPTION OF THE INVENTION

Technical Problem

The present inventors have attempted to provide a pharmaceutical preparation that is dissolved immediately in gastric juice, thereby exhibiting a rapid effect, at the same time while solving the problem that omeprazole is unstable at a low pH.

Therefore, the present inventors developed a preparation in which omeprazole is immediately dissolved after the pH of the acidic gastric juice is neutralized by adjusting the dissolution pattern of these active ingredients in a combination preparation comprising omeprazole and sodium bicarbonate. Based on the above, the present inventors completed the present invention.

Solution to Problem

The present invention provides a pharmaceutical preparation comprising omeprazole, an enantiomer thereof or a pharmaceutically acceptable salt thereof; and sodium bicarbonate, characterized in that the omeprazole, the enantiomer thereof or the pharmaceutically acceptable salt thereof is in the form of a pellet or a granule, and when the preparation is dissolved in a solution, sodium bicarbonate is first dissolved, and then the omeprazole, the enantiomer thereof or the pharmaceutically acceptable salt thereof is dissolved.

In the present invention, the "pellet" may be prepared by spraying a coating solution comprising an active ingredient or an excipient on white sugar sphere.

In the present invention, the "granule" may be prepared using a wet granulation method using a binder solution or a dry granulation method without using a binder solution.

In one embodiment, the pellet or granule may comprise 30% or less of sodium bicarbonate based on the total weight of sodium bicarbonate comprised in the preparation. Preferably, omeprazole is present in the form of a granule, and when prepared by a wet granulation method, the omeprazole granule may comprise 30% or less of sodium bicarbonate based on the total weight of sodium bicarbonate comprised in the preparation.

In one embodiment, the pellet or granule may be coated with a coating agent, and may not comprise sodium bicarbonate.

In another embodiment, the coating agent may be at least one selected from the group consisting of polyvinyl alcohol, povidone, hydroxypropyl cellulose, hydroxypropyl methyl cellulose, polyvinyl acetate, ethyl cellulose, and dimethylaminoethyl methacrylate•methyl methacrylate copolymer.

In addition, the present invention provides the pharmaceutical preparation, wherein when the preparation is dissolved in a solution at pH 1.2 by a flow through cell (FTC) dissolution test method, the ratio of the time for the solution to reach a pH of 6.5 with respect to the time to reach the highest concentration of the omeprazole, the enantiomer thereof or the pharmaceutically acceptable salt thereof is less than 1.

Specifically, since omeprazole, an enantiomer thereof or a pharmaceutically acceptable salt thereof is stable in an environment of pH 5.0, preferably pH 6.0, and more preferably pH 6.5 or higher, it is preferred that the solution reaches pH 6.5, and then the concentration of omeprazole, an enantiomer thereof or a pharmaceutically acceptable salt thereof reaches the highest.

The flow through cell dissolution test method of the present invention is defined as a dissolution test method for solid preparations in USP apparatus 4, and is a dissolution test method in which a drug is fixed in a cell and a test solution passes through the cell. It refers to a dissolution test method that can confirm the release rate of a drug while maintaining a sink condition similar to an in vivo condition since a pH of a test solution can be immediately changed.

In addition, the present invention provides the pharmaceutical preparation, in which the time to reach the highest concentration of the omeprazole, the enantiomer thereof or the pharmaceutically acceptable salt thereof is within 20 minutes when the preparation is dissolved in a solution at pH 1.2 by a flow through cell dissolution test method. Preferably, the time to reach the highest concentration of the omeprazole, the enantiomer thereof or the pharmaceutically acceptable salt thereof may be between 5 minutes and 15 minutes.

In addition, the present invention provides the pharmaceutical preparation, in which the pH in the stomach increases within 50 minutes after the single administration of the preparation. Preferably, the pH in the stomach may increase within 45 minutes after the single administration.

In the present invention, the omeprazole, the enantiomer thereof or the pharmaceutically acceptable salt thereof may be esomeprazole.

In addition, in the present invention, the omeprazole, the enantiomer thereof or the pharmaceutically acceptable salt thereof may be esomeprazole magnesium salt.

In addition, in the present invention, the omeprazole, the enantiomer thereof or the pharmaceutically acceptable salt thereof may be esomeprazole magnesium trihydrate.

The present invention provides a method for preparing a pharmaceutical preparation comprising omeprazole, an enantiomer thereof or a pharmaceutically acceptable salt thereof; and sodium bicarbonate, the method comprising the steps of:
  (a) coating a core with a first coating solution comprising omeprazole, an enantiomer thereof or a pharmaceutically acceptable salt thereof to prepare a first coated product;
  (b) coating the first coated product with a second coating solution comprising a coating agent to prepare a second coated product;
  (c) mixing the second coated product with sodium bicarbonate to obtain a mixture;
  (d) tableting the mixture to obtain an uncoated tablet; and
  (e) coating the uncoated tablet with a third coating solution and then drying to obtain a coated tablet. In one embodiment, in step (c), sodium bicarbonate is wet granulated and then mixed with the coated product. In another embodiment, the core may be white sugar sphere.

The coating agent of the present invention may be at least one selected from the group consisting of polyvinyl alcohol, povidone, hydroxypropyl cellulose, hydroxypropyl methyl cellulose, polyvinyl acetate, ethyl cellulose, and dimethylaminoethyl methacrylate•methyl methacrylate copolymer, but is not limited thereto.

In addition, the present invention provides a method for preparing a pharmaceutical preparation comprising omeprazole, an enantiomer thereof or a pharmaceutically acceptable salt thereof; and sodium bicarbonate, the method comprising the steps of:
  (a) mixing omeprazole, an enantiomer thereof or a pharmaceutically acceptable salt thereof with sodium bicarbonate to obtain a mixture;
  (b) kneading the mixture with a binder solution to obtain a kneaded product;
  (c) mixing the kneaded product with sodium bicarbonate to obtain a final mixture;
  (d) tableting the final mixture to obtain an uncoated tablet; and
  (e) coating the uncoated tablet with a coating solution and then drying to obtain a coated tablet,
  wherein the content of sodium bicarbonate mixed in the step (a) is 0 to 75% by weight or less based on the total weight of sodium bicarbonate comprised in the preparation. Preferably, the content of sodium bicarbonate mixed in the step (a) is 30% by weight or less based on the total weight of sodium bicarbonate comprised in the preparation.

In addition, the present invention provides a method for preparing a pharmaceutical preparation comprising omeprazole, an enantiomer thereof or a pharmaceutically acceptable salt thereof; and sodium bicarbonate, the method comprising the steps of:
  (a) mixing omeprazole, an enantiomer thereof or a pharmaceutically acceptable salt thereof with sodium bicarbonate to obtain a mixture;
  (b) slugging the mixture to obtain a slugged product;
  (c) mixing the slugged product with sodium bicarbonate to obtain a final mixture;
  (d) tableting the final mixture to obtain an uncoated tablet; and
  (e) coating the uncoated tablet with a coating solution and then drying to obtain a coated tablet.

The present invention relates to the method for preparing a pharmaceutical preparation, in which when the preparation is dissolved in a solution at pH 1.2 by a flow through cell dissolution test method, the ratio of the time for the solution to reach a pH of 6.5 with respect to the time to reach the highest concentration of the omeprazole, the enantiomer thereof or the pharmaceutically acceptable salt thereof is less than 1.

In addition, the present invention relates to the method for preparing a pharmaceutical preparation, in which when the preparation is dissolved in a solution at pH 1.2 by a flow through cell dissolution test method, the time to reach the highest concentration of the omeprazole, the enantiomer thereof or the pharmaceutically acceptable salt thereof is within 20 minutes. Preferably, the time to reach the highest concentration of the omeprazole, the enantiomer thereof or the pharmaceutically acceptable salt thereof may be between 5 minutes and 15 minutes.

In addition, the present invention provides the method for preparing a pharmaceutical preparation, in which the pH in the stomach increases within 50 minutes after the single administration of the preparation. Preferably, the pH in the stomach may increase within 45 minutes after the single administration.

Effect of the Invention

The present invention relates to a pharmaceutical preparation comprising omeprazole, an enantiomer thereof or a pharmaceutically acceptable salt thereof, and sodium bicarbonate, in which the release pattern is adjusted so that sodium bicarbonate is first dissolved so as to prevent the degradation of omeprazole.

The present invention provides a pharmaceutical preparation in which sodium bicarbonate is first dissolved in a solution from a combination preparation of omeprazole and sodium bicarbonate so as to raise a pH of the solution, and then omeprazole is dissolved such that the degradation of omeprazole is prevented and thus the bioavailability of a drug is elevated, and omeprazole can exhibit a maximum dissolution rate within 20 minutes after administration, thereby exhibiting an immediate effect.

BEST MODE FOR CARRYING OUT THE INVENTION

Hereinafter, the present invention is to be described in more detail through the following examples. However, these examples are merely provided for a better understanding of the present invention for the purpose of illustration, but are not intended to limit the scope of the present invention.

Example 1

Preparation of Combination Tablet of Esomeprazole and Sodium Bicarbonate (Pellet)

The tablets of Example 1 were prepared according to the following preparation method.

1. First Pellet Coating

Hydroxypropyl cellulose was added and dissolved in purified water, and then arginine, simethicone, esomeprazole magnesium trihydrate (20 mg to 40 mg as esomeprazole), magnesium oxide, and talc were added and dispersed to prepare a first coating solution. White sugar sphere was added to a fluidized bed coating machine, and the first coating solution was sprayed to perform a first pellet coating process (first coated product).

2. Second Pellet Coating

Purified water, polyvinyl alcohol, talc, titanium oxide, glycerol monocaprylocaprate, and sodium lauryl sulfate were added to the preparation tank and dispersed to prepare a second coating solution. The first coated product was added to a fluidized bed coating machine, and the second coating solution was sprayed to perform a second pellet coating process (second coated product).

3. Post Mixing (Simple Mixing Method)

The second coated product was added to a mixing machine, and sodium bicarbonate (800 mg) was added. In this case, purified water may be included depending on the moisture content. Further, copovidone, crospovidone and sodium stearyl fumarate were added thereto and mixed (final mixture).

4. Tableting

The final mixture was tableted by a tablet press machine (uncoated tablet).

5. Third Coating

Polyvinyl alcohol, talc, titanium oxide, glycerol monocaprylocaprate, sodium lauryl sulfate, red iron oxide, black iron oxide, yellow iron oxide, and purified water were added to the preparation tank and dissolved to prepare a third coating solution. The uncoated tablets were added to a coating machine, and coated with the third coating solution, and then dried to obtain the coated tablets.

Example 2

Preparation of Combination Tablet of Esomeprazole and Sodium Bicarbonate (Pellet)

The tablets of Example 2 were prepared according to the preparation method of Example 1 above, and a wet granulation process was used instead of simple mixing in the post mixing process of step 3 in the preparation method.

3. Post Mixing (Wet Granulation Method)

A binder solution was prepared with copovidone and water in a separate container, and then kneaded with sodium bicarbonate (800 mg), and dried to prepare a kneaded product. Thereafter, the kneaded product and the second coated product were added to a mixing machine, and copovidone, crospovidone, and sodium stearyl fumarate were added and mixed (final mixture).

Example 3

Preparation of Combination Tablet of Esomeprazole and Sodium Bicarbonate (Wet Granulation)

The tablets of Example 3 (20 mg to 40 mg of esomeprazole, 800 mg of sodium bicarbonate) were prepared according to the following preparation method.

1. Mixing

Esomeprazole magnesium trihydrate, microcrystalline cellulose, and sodium bicarbonate were added and mixed by a High Speed Mixer.

2. Kneading

Hydroxypropyl cellulose was added and dissolved in purified water to prepare a binder solution. The binder solution was added to the mixture and kneaded.

3. Final Mixing and Lubricating

The kneaded product, sodium bicarbonate, copovidone, and croscarmellose sodium were added to a mixing machine and mixed, and then sodium stearyl fumarate was added and lubricated to prepare a final mixture.

4. Tableting and Coating

The final mixture was tableted by a tablet press machine (uncoated tablet). Polyvinyl alcohol, titanium oxide, polyethylene glycol, talc and purified water were added to the preparation tank and dissolved. The uncoated tablets were added to a coating machine, coated, and then dried to obtain the coated tablets.

Example 4

Preparation of Combination Tablet of Esomeprazole and Sodium Bicarbonate (Dry Granulation)

The tablets of Example 4 (20 mg to 40 mg of esomeprazole, 800 mg of sodium bicarbonate) were prepared according to the following preparation method.

1. Mixing and Lubricating

Esomeprazole magnesium trihydrate, sodium bicarbonate, magnesium oxide, and crospovidone were added and mixed, and then sodium stearyl fumarate was added and lubricated to obtain a mixture.

2. Slugging

The mixture was slugged by a slugging machine.

3. Final Mixing and Lubricating

The slugged product, sodium bicarbonate, copovidone and crospovidone were added and mixed, and then sodium stearyl fumarate was added and lubricated to obtain a final mixture.

4. Tableting and Coating

The final mixture was tableted by a tablet press machine (uncoated tablet). Hydroxypropyl methyl cellulose, titanium oxide, polyethylene glycol, and purified water were added to the preparation tank and dissolved. The uncoated tablets were added to a coating machine, coated, and then dried to obtain the coated tablets.

Test Example 1

Comparative Dissolution Test of Tablet

The dissolution test was performed on the tablets of Examples 1, 3 and 4 (20 mg of esomeprazole/800 mg of sodium bicarbonate) prepared above, and the dissolution test and analysis conditions are as follows.

<Dissolution Test Condition>
1) Dissolution method: the Korean Pharmacopoeia, General tests, Dissolution test, Method 3 (Flow Through Cell Method)
2) Dissolution medium: pH 1.2→pH 4.0→pH 6.8
3) Dissolution temperature: 37±0.5° C.
4) Flow rate: 2 mL/min
5) Test time: pH 1.2 (15 minutes)→pH 4.0 (15 minutes) →pH 6.8 (30 minutes)
6) Cell size: 22.4 mm <HPLC Analysis Condition>
1) Detector: UV spectrophotometer (measurement wavelength: 302 nm)
2) Column: Capcell Pak C18 (4.6×150 mm, 5 μm) or a column equivalent thereto
3) Injection amount: 20 μL
4) Flow rate: 1.0 mL/min
5) Column temperature: constant temperature near 30° C.
6) Sample temperature: constant temperature near 10° C.

7) Mobile phase: a mixture of acetonitrile, a buffer solution at pH 7.3*, and water (350:500:150)

\* The buffer solution at pH 7.3 was prepared as follows: 1 mol/L sodium dihydrogen phosphate solution and 0.5 mol/L disodium hydrogen phosphate solution were taken in 10.5 mL and 60 mL, respectively, to be put in an 1 L volumetric flask, followed by filling the flask with purified water up to the calibration mark.

The results of the dissolution test, and the results of esomeprazole concentration (ng/mL) and the pH change of the solution are shown in Table 1 below and FIGS. 1 to 3.

TABLE 1

| | (Concentration ng/mL) | | | | | |
|---|---|---|---|---|---|---|
| Time | Example 1 | | Example 3 | | Example 4 | |
| (min) | Concentration | pH | Concentration | pH | Concentration | pH |
| 0 | 0 | 0 | 0 | 0 | 0 | 0 |
| 2.5 | 202.78 | 5.5 | 295.72 | 4.1 | 231.61 | 4.3 |
| 5.0 | 406.47 | 7.4 | 636.09 | 6.9 | 318.06 | 8.6 |
| 7.5 | 562.32 | 7.1 | 586.48 | 6.9 | 309.97 | 7 |
| 10.0 | 784.79 | 6.8 | 554.86 | 6.8 | 293.27 | 6.8 |
| 12.5 | 675.5 | 6.6 | 493.97 | 6.6 | 283.83 | 6.6 |
| 15.0 | 590.3 | 6.5 | 439.15 | 6.5 | 277.46 | 6.5 |
| 20.0 | 449.34 | 6 | 302.99 | 6 | 247.03 | 5.9 |
| 25.0 | 265.89 | 4.4 | 116.18 | 4.4 | 219.63 | 4.4 |
| 30.0 | 161.48 | 4.9 | 41.49 | 4.9 | 151.57 | 4.9 |
| 35.0 | 107.6 | 4.9 | 24.4 | 4.7 | 58.18 | 4.9 |
| 40.0 | 68.28 | 4.7 | 27.32 | 4.8 | 20.85 | 4.9 |
| 45.0 | 64.06 | 4.9 | 39.93 | 4.9 | 12.33 | 4.9 |
| 50.0 | 43.81 | 4.7 | 39.44 | 4.5 | 13.8 | 4.7 |
| 55.0 | 26.08 | 4.4 | 37.29 | 4.4 | 20.13 | 4.5 |
| 60.0 | 21.33 | 4.3 | 37.31 | 4.2 | 19.9 | 4.3 |

Figure 1:
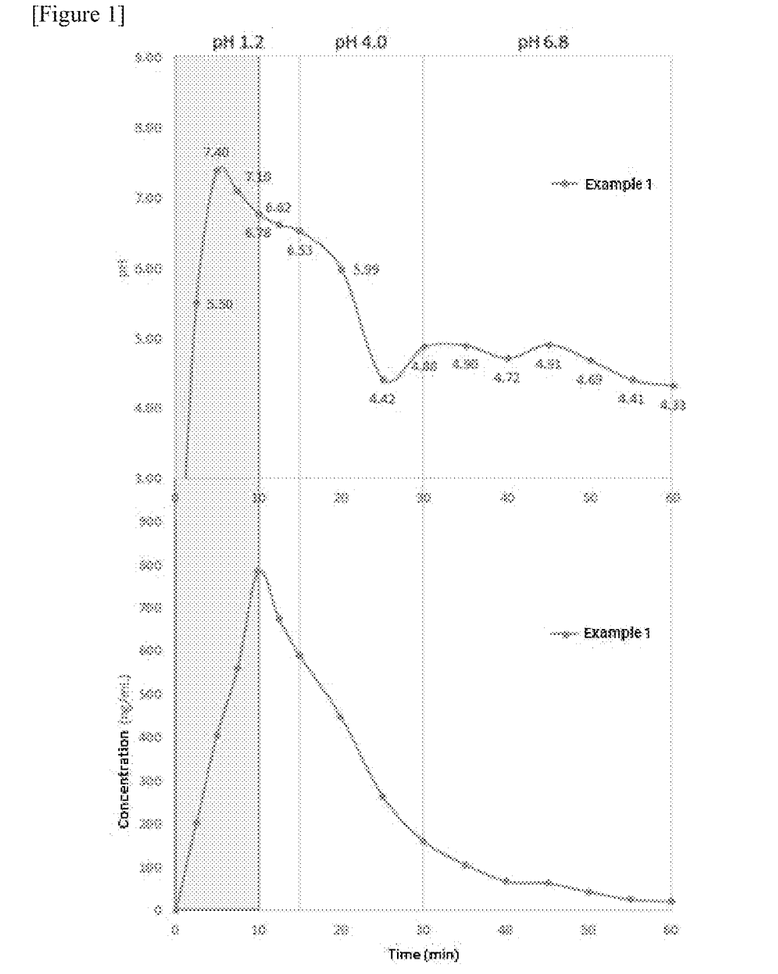
FIG. 1 is a graph showing the dissolution rate and pH change over time in Example 1.
Figure 2:
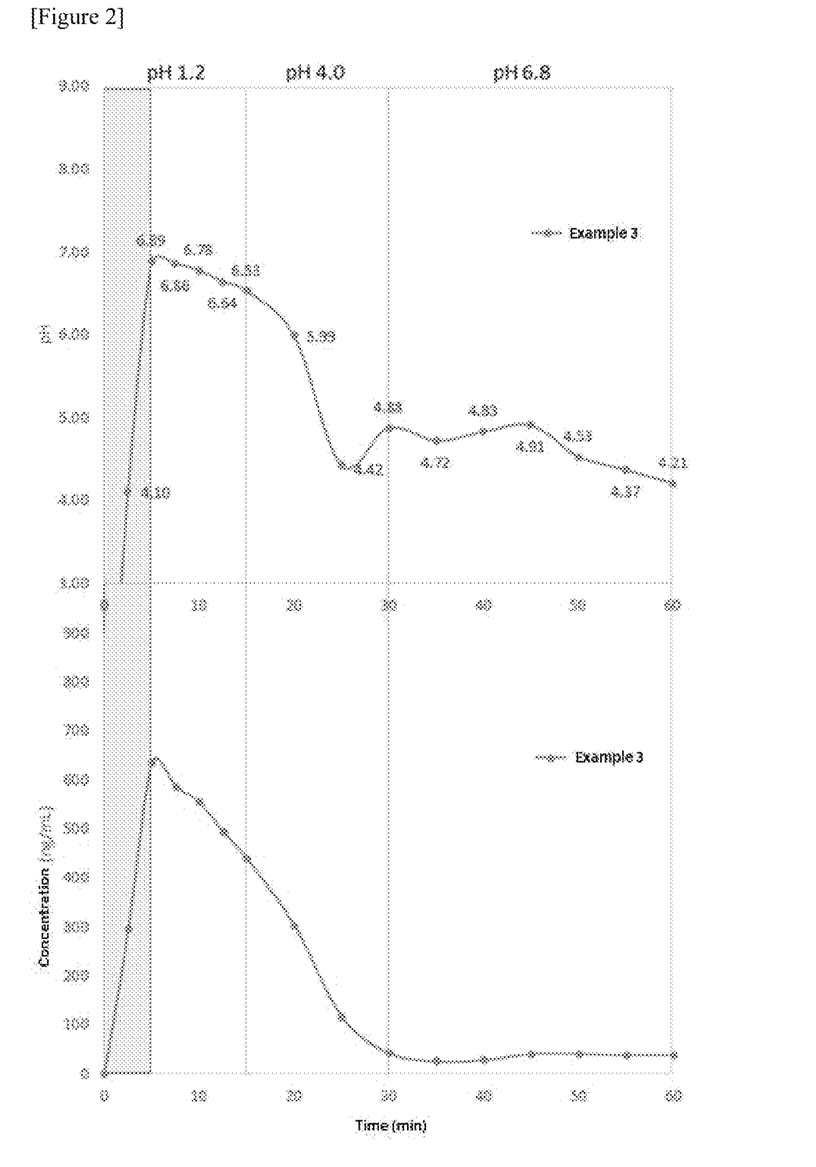
FIG. 2 is a graph showing the dissolution rate and pH change over time in Example 3.
Figure 3:
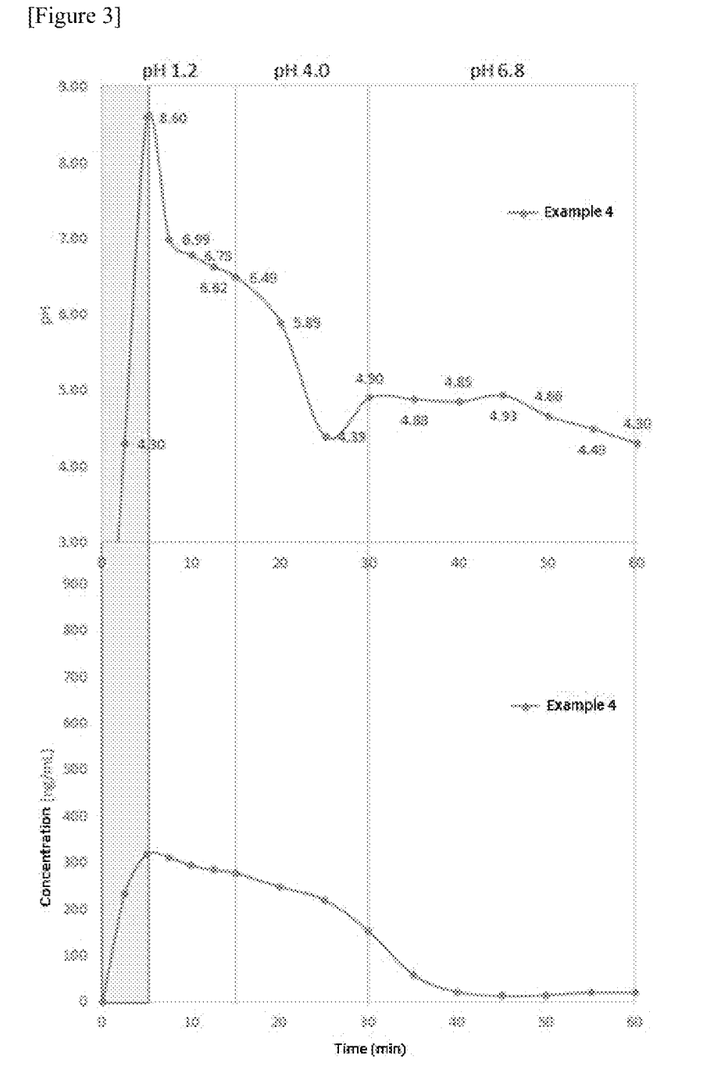
FIG. 3 is a graph showing the dissolution rate and pH change over time in Example 4.

As shows in Table 1 above and FIGS. 1 to 3, it was confirmed that, in the tablets of Examples 1, 3 and 4, the time to reach the highest concentration of esomeprazole was about 10 minutes (Example 1), about 5 minutes (Example 3), and about 5 minutes (Example 4), respectively, and the time to reach a pH of 6.5 was all less than 5 minutes. Therefore, in the tablets of Examples 1 to 3, it was confirmed that the ratio of the time for the solution to reach a pH of 6.5 with respect to the time to reach the highest concentration of omeprazole was all less than 1.

However, it was confirmed that the maximum esomeprazole concentration was the highest in Example 1. This is due to the properties of esomeprazole that is easily degraded under acidic conditions, and it can be seen that a tablet having the release pattern, in which sodium bicarbonate is first released, and esomeprazole is rapidly released after the gastric acid is neutralized, will exhibit the most excellent drug efficacy. Therefore, it can be seen that the tablet of Example 1 first reached a pH of 6.5 between 2.5 and 5.0 minutes after administration, and reached the maximum esomeprazole concentration after 10 minutes, and thus exhibited the most excellent release pattern.

As a result, sodium bicarbonate should be rapidly disintegrated, and even in this case, sodium bicarbonate is disintegrated, and esomeprazole is released after a certain period of time to reach the maximum concentration, thereby exhibiting excellent effects.

Test Example 2

Results of Clinical Trial of a Combination of Esomeprazole and Sodium Bicarbonate In order to compare and evaluate the pharmacokinetic and pharmacodynamic properties and safety after the single administration and the repeated administration of the tablets of Example 1 (20 mg of esomeprazole/800 mg of sodium bicarbonate) and Nexium tablets (D027 20 mg) to healthy adults, the clinical trial was performed in a randomized, open-labeled, repeated administration, 2×2 crossover design as shown in Table 2 below.

TABLE 2

| Group | Number of subjects | Period 1 | Period 2 | Washout |
|---|---|---|---|---|
| A | 20 | T | R | at least 7 days or more |
| B | 20 | R | T | at least 7 days or more |

T: 1 tablet of Example 1, repeated orally administered once a day for 7 days under fasting conditions
R: 1 tablet of D027 20 mg, repeated orally administered once a day for 7 days under fasting conditions All subjects were supposed to take the investigational drug (R or T) at the same time in the morning, about 1 hour later, start the given standard meal (700-800 kcal, containing 5-25% fat), and end the meal within 20 minutes.

Subjects were subjected to baseline pH monitoring for 24 hours in Period 1, and then administered with the investigational drug once a day for a total of 7 days according to the each assigned group from the first day of Period 1. All subjects were supposed to start the given standard meal about 1 hour after administration of the investigational drug and end the meal within 20 minutes.

The pH monitoring and pharmacokinetic blood collection for 24 hours after the single administration were performed on the first day of Period 1, and the pH monitoring and pharmacokinetic blood collection for 24 hours after the repeated administration were performed on the 7th day of Period 1, and all subjects were discharged on the 8th day. After the last dose of Period 1, subjects were subjected to washout for 7 days or more, and then were hospitalized again, and Period 2 of clinical trial was performed.

Figure 4:
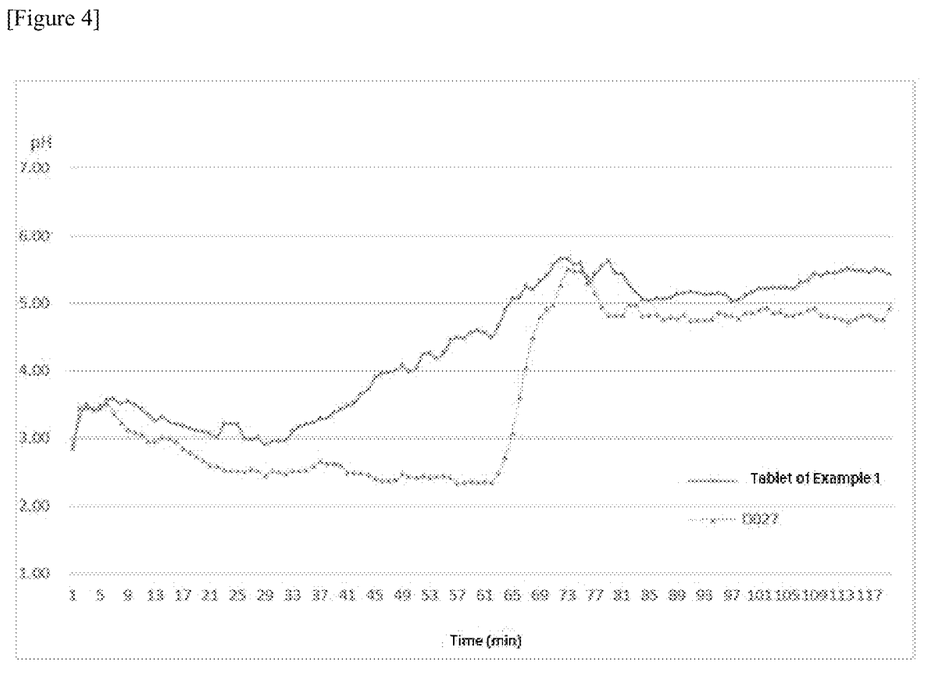
FIG. 4 is a graph showing the average pH value after the single administration of the test drug and the reference drug.
Figure 5:
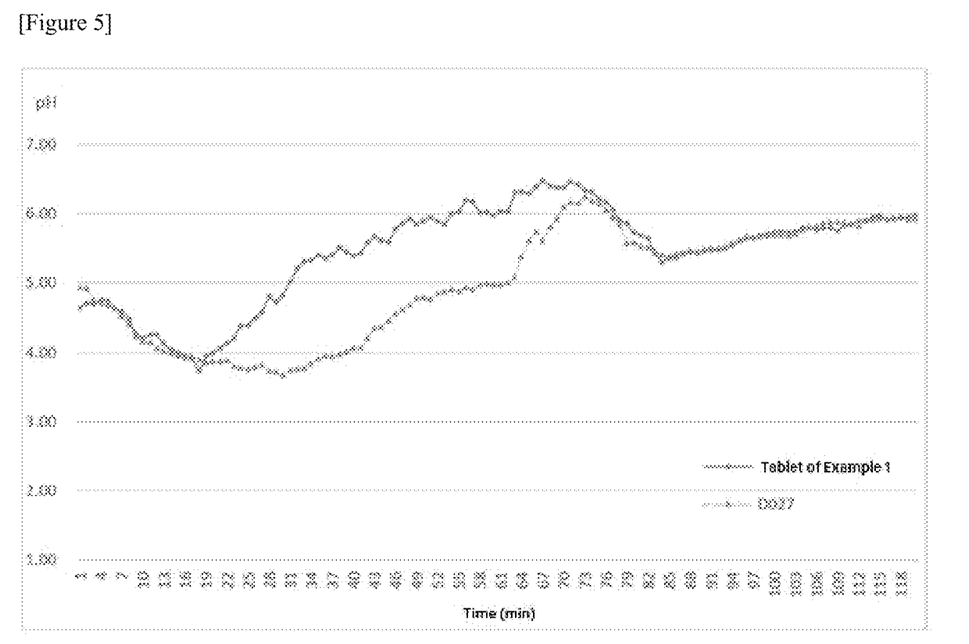
FIG. 5 is a graph showing the average pH value after the repeated administration of the test drug and the reference drug.

After the single administration and after the repeated administration, the average pH value in minutes is shown in FIGS. 4 and 5. As shows in FIG. 4, it was confirmed that the pH increased from about 30 minutes after the single dose of the tablet of Example 1, whereas the pH increased from 1 hour after the single dose of the reference drug.

In addition, as shows in FIG. 5, it was confirmed that the pH increased from about 20 minutes after the repeated dose of the tablet of Example 1, whereas the pH gradually increased from 30 minutes after the repeated dose of the reference drug.

As a result, as confirmed in Test Example 1, it can be seen that the tablet of Example 1 rapidly raises the pH in the stomach when administered.

Test Example 3

Comparative Dissolution Rate Test According to Content of Sodium Bicarbonate in Esomeprazole Granules The following test was performed to confirm the appropriate % by weight of sodium bicarbonate comprised in esomeprazole granules.

According to the preparation method of Example 3 above, the tablets of Examples 5 to 10 were prepared, but in step <1. mixing> of Example 3, when preparing esomeprazole granules, the tablets comprising 0, 10, 30, 40, 50 and 75% by weight of sodium bicarbonate based on the weight (800 mg) of sodium bicarbonate of the whole tablet were prepared. A dissolution test was performed on the tablets of Examples 5 to 10 prepared above, and the dissolution test and analysis conditions are as follows.

<Dissolution Test Condition>
1) Dissolution method: the Korean Pharmacopoeia, General tests, Dissolution test, Method 3 (Flow Through Cell Method)
2) Dissolution medium: pH 1.2→pH 4.0
3) Dissolution temperature: 37±0.5° C.
4) Flow rate: 2 mL/min
5) Test time: pH 1.2 (15 minutes)→pH 4.0 (30 minutes)
6) Cell size: 22.4 mm <HPLC Analysis Condition>
1) Detector: UV spectrophotometer (measurement wavelength: 302 nm)
2) Column: Capcell Pak C18 (4.6×150 mm, 5 μm) or a column equivalent thereto
3) Injection amount: 20 μL
4) Flow rate: 1.0 mL/min
5) Column temperature: constant temperature near 30° C.
6) Sample temperature: constant temperature near 10° C.
7) Mobile phase: a mixture of acetonitrile, a buffer solution at pH 7.3*, and water (350:500:150)

* The buffer solution at pH 7.3 was prepared as follows: 1 mol/L sodium dihydrogen phosphate solution and 0.5 mol/L disodium hydrogen phosphate solution were taken in 10.5 mL and 60 mL, respectively, to be put in an 1 L volumetric flask, followed by filling the flask with purified water up to the calibration mark.

Figure 6:
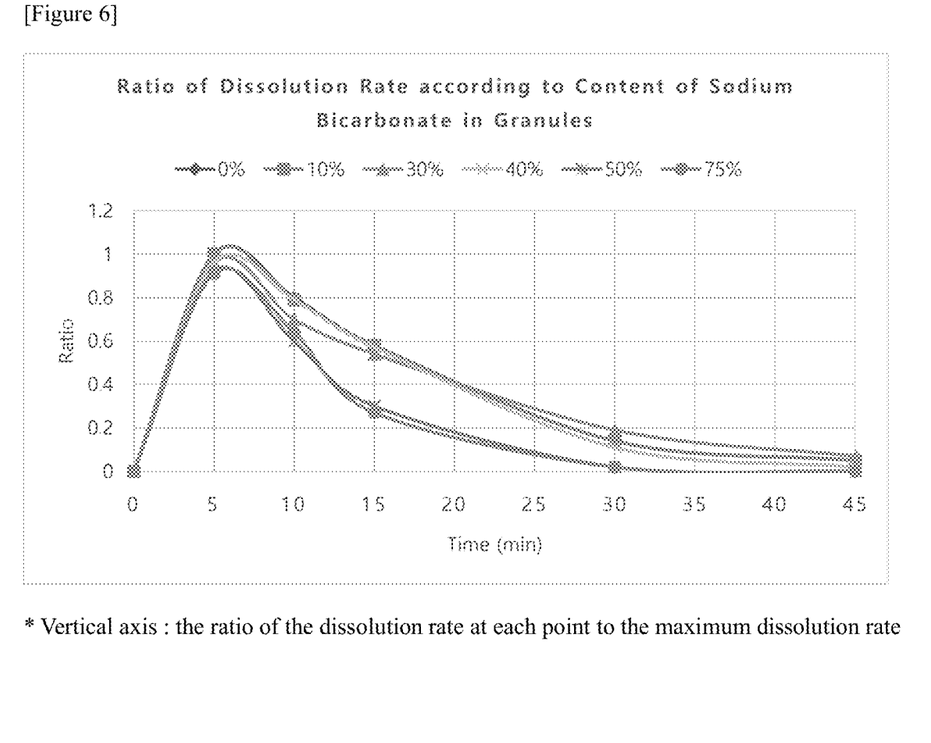
FIG. 6 is a graph showing the ratio of dissolution rate according to the content of sodium bicarbonate in esomeprazole granules.
Figure 7:
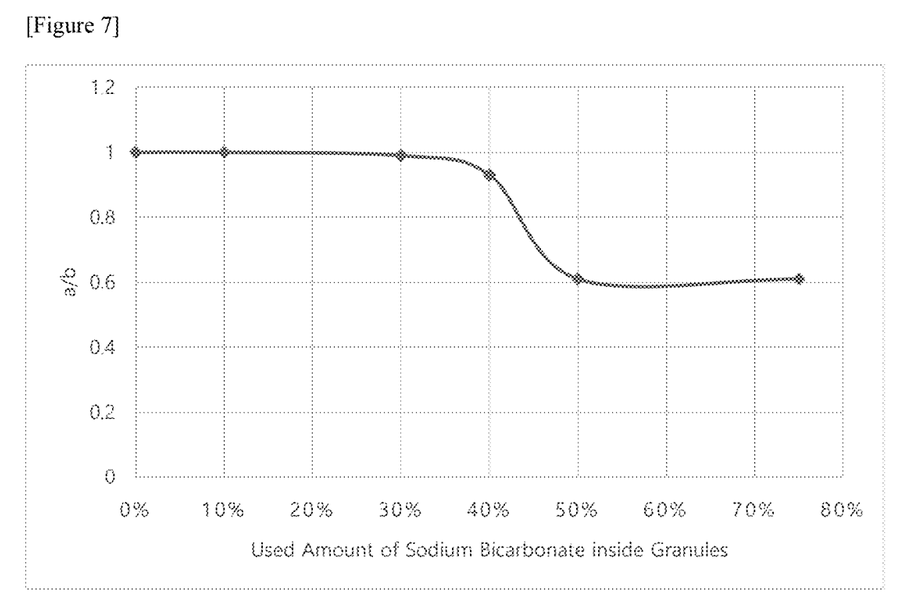
FIG. 7 is a graph showing the ratio of AUC (area under the curve) of dissolution rate according to the content of sodium bicarbonate in esomeprazole granules.

The results of the dissolution test are shown in Table 3, and FIGS. 6 and 7.

TABLE 3

| | | Example 5 | Example 6 | Example 7 | Example 8 | Example 9 | Example 10 |
|---|---|---|---|---|---|---|---|
| % by weight of sodium bicarbonate in granules | | 0 | 10 | 30 | 40 | 50 | 75 |
| % by weight of sodium bicarbonate in post mixing | | 100 | 90 | 70 | 60 | 50 | 25 |
| Esomeprazole concentration* | 5 minutes | 1.00 | 1.00 | 0.96 | 0.96 | 0.92 | 0.91 |
| | 10 minutes | 0.80 | 0.79 | 0.70 | 0.79 | 0.60 | 0.64 |
| | 15 minutes | 0.58 | 0.58 | 0.54 | 0.57 | 0.30 | 0.27 |
| | 30 minutes | 0.14 | 0.14 | 0.19 | 0.11 | 0.02 | 0.02 |
| | 45 minutes | 0.05 | 0.05 | 0.07 | 0.02 | 0.00 | 0.00 |
| AUC | | 16.29 | 16.24 | 16.15 | 15.07 | 9.89 | 9.84 |
| a/b** | | 1.00 | 1.00 | 0.99 | 0.93 | 0.61 | 0.61 |

*The concentration of esomeprazole is expressed as a ratio of the dissolution rate (ng/mL) at each time point with respect to the dissolution rate (ng/mL) at 5 minutes of the tablet of Example 5.
**b is the AUC (area under the curve) of the dissolution rate of Example 5, and a represents the AUC of each of Examples 5 to 10.

As shown in Table 3 above, it was confirmed that the AUC was reduced in Examples 8 to 10 comprising more than 30% by weight of sodium bicarbonate in the granules based on the weight (800 mg) of sodium bicarbonate of the whole tablet. Therefore, it can be seen that it is suitable to use 30% by weight or less of sodium bicarbonate inside the granules based on the weight (800 mg) of sodium bicarbonate of the whole tablet.

The invention claimed is:

1. A tablet comprising:
   esomeprazole or a pharmaceutically acceptable salt thereof in the form of a pellet; and
   sodium bicarbonate;
   wherein:
   the amount of esomeprazole or the pharmaceutically acceptable salt thereof is 20 mg to 40 mg as esomeprazole;
   the total amount of sodium bicarbonate in the tablet is 800 mg;
   the pellet comprises a first quantity of sodium bicarbonate, which comprises up to 30% by weight of the total weight of the sodium bicarbonate in the tablet;
   the tablet is prepared by mixing the pellet with a second quantity of sodium bicarbonate or a granule comprising the second quantity of sodium bicarbonate, wherein the second quantity of sodium bicarbonate comprises 70% by weight or more of the total weight of the sodium bicarbonate in the tablet;
   when the tablet is dissolved in a solution, the second quantity of sodium bicarbonate is first dissolved, and then the esomeprazole, or the pharmaceutically acceptable salt thereof is dissolved;
   the tablet dissolves immediately in gastric juice;
   when the tablet is singly administered orally to a subject, the pH in the stomach of the subject increases within 45 minutes; and when the tablet is dissolved in a solution at pH 1.2 by a flow through cell dissolution test method, the ratio of the time for the solution to reach a pH of 6.5 with respect to the time to reach the highest concentration of the esomeprazole or the pharmaceutically acceptable salt thereof is less than 1, and the time to reach the highest concentration of the esomeprazole or the pharmaceutically acceptable salt thereof is within 20 minutes.

2. The tablet according to claim 1, characterized in that the pellet comprising the esomeprazole or the pharmaceutically acceptable salt thereof is coated with a coating agent, and does not comprise sodium bicarbonate.

3. The tablet according to claim 2, characterized in that the coating agent is selected from the group consisting of polyvinyl alcohol, povidone, hydroxypropyl cellulose, hydroxypropyl methyl cellulose, polyvinyl acetate, ethyl cellulose, and dimethylaminoethyl methacrylate•methyl methacrylate copolymer, or a combination thereof.

4. The tablet according to claim 1, characterized in that the time to reach the highest concentration of the esomeprazole or the pharmaceutically acceptable salt thereof is between 5 minutes and 15 minutes.

5. The tablet according to claim 1, characterized in that the esomeprazole or the pharmaceutically acceptable salt thereof is esomeprazole.

6. The tablet according to claim 1, characterized in that the esomeprazole or the pharmaceutically acceptable salt thereof is esomeprazole magnesium salt.

7. The tablet according to claim 1, characterized in that the esomeprazole or the pharmaceutically acceptable salt thereof is esomeprazole magnesium trihydrate.

* * * * *